(12) United States Patent
Prichard (10) Patent No.: US 10,471,112 B2
(45) Date of Patent: Nov. 12, 2019

(54) CANNABINOID ENRICHED CREAMER COMPOSITION

(71) Applicant: Anthony C. Prichard, Englewood, CO (US)

(72) Inventor: Anthony C. Prichard, Englewood, CO (US)

( * ) Notice: Subject to any disclaimer, the term of this patent is extended or adjusted under 35 U.S.C. 154(b) by 0 days.

(21) Appl. No.: 15/675,709

(22) Filed: Aug. 12, 2017

(65) Prior Publication Data

US 2019/0046596 A1   Feb. 14, 2019

(51) Int. Cl.
| | | |
|---|---|---|
| *A61K 36/00* | (2006.01) |
| *A61K 36/185* | (2006.01) |
| *A61K 9/00* | (2006.01) |
| *A61K 47/44* | (2017.01) |
| *A61K 47/46* | (2006.01) |
| *A61K 47/24* | (2006.01) |
| *A61K 31/05* | (2006.01) |
| *A23C 11/10* | (2006.01) |
| *A23F 3/40* | (2006.01) |
| *A23F 5/46* | (2006.01) |
| *A23L 2/52* | (2006.01) |
| *A23C 11/04* | (2006.01) |
| *A61K 36/889* | (2006.01) |
| *A61K 36/898* | (2006.01) |
| *A61K 36/28* | (2006.01) |

(52) U.S. Cl.
CPC ............ *A61K 36/185* (2013.01); *A23C 11/04* (2013.01); *A23C 11/10* (2013.01); *A23F 3/40* (2013.01); *A23F 3/405* (2013.01); *A23F 5/46* (2013.01); *A23L 2/52* (2013.01); *A61K 9/0095* (2013.01); *A61K 31/05* (2013.01); *A61K 36/28* (2013.01); *A61K 36/889* (2013.01); *A61K 36/898* (2013.01); *A61K 47/24* (2013.01); *A61K 47/44* (2013.01); *A61K 47/46* (2013.01); *A23V 2002/00* (2013.01)

(58) Field of Classification Search
None
See application file for complete search history.

*Primary Examiner* — Qiuwen Mi
(74) *Attorney, Agent, or Firm* — Roger A. Jackson (57) ABSTRACT

The present invention is a cannabinoid enriched creamer composition and kit for human consumption, the composition includes by weight about thirty-five point three-three percent (35.33%) coconut oil, about thirteen point five-eight percent (13.58%) ghee, about thirty-two point six percent (32.6%) goats milk powder, about five point eight-five percent (5.85%) vanilla powder, about one point three-four percent (1.34%) stevia extract, about point three-eight percent (0.38%) sunflower lecithin, and about ten point nine two percent (10.92%) cannabinoid in a liquid state.

7 Claims, 6 Drawing Sheets

CANNABINOID ENRICHED CREAMER COMPOSITION

RELATED PATENT APPLICATIONS

There are no related patent applications.

FIELD OF THE INVENTION

The present invention generally relates to a composition that combines creamer and a cannabinoid and further a kit for making a creamer and cannabinoid composition for human consumption. More particularly the present invention composition utilizes a variety of consumable modifiers for the creamer composition that improve flavor, give a smoother texture, promote easier digestion, gives energy, has anti-oxidant properties, having vitamins, is a detoxifier, is anti-inflammatory, having minerals, and the like, in addition to oil from industrial hemp plants being preferably in particular non-psychoactive cannabinoids such as cannabidiol.

DESCRIPTION OF THE RELATED ART

Looking in particular at the coffee/cannabinoid prior art in U.S. Pat. No. 9,565,865 to Bhairam '865, disclosed is a method for making a coffee product, comprising: (a) extracting cannabinoids using liquid carbon dioxide to yield a cannabis carbon dioxide extract containing cannabinoids; (b) evaporating or purging the carbon dioxide from the cannabis carbon dioxide extract containing cannabinoids; (c) heating the cannabis extract containing cannabinoids at an elevated temperature to yield a heated cannabis extract containing cannabinoids; (d) heating the extract containing cannabinoids with propylene glycol, or mixing the extract containing cannabinoids with maltodextrin to provide an extract containing cannabinoids and propylene glycol or maltodextrin; and (e) admixing the extract containing cannabinoids and propylene glycol or maltodextrin into coffee beans to provide said coffee product. Note that Bhairam '865 is related to the actual coffee product medium itself (K-CUPS), and a specific method of cannabinoid extraction (CO2), using maltodextrin (synthetic food starch) and propylene glycol (RV Antifreeze).

Continuing, in the coffee/cannabinoid prior art in United States Patent Application Publication Number 2015/0352044 to Benson, et al. disclosed are single-serve containers for use in brewing a cannabis-based beverage are described, as are methods for preparing a single-serve container configured for receipt in a single-serve brewing machine. The method in Benson includes: adding a processed cannabis product to the single-serve container; also adding, to the single-serve container, at least one of an extraction or flavoring agent; and sealing the single-serve container. Benson is more concerned with K-CUP manufacture with added flavorings, plus a process of decarboxylating from cannabis.

Further, in the coffee/cannabinoid prior art in United States Patent Application Publication Number 2017/0112161 to Bhairam '161 disclosed are methods of making coffee products containing cannabinoids that are extracted from the Cannabis plant. According to one embodiment in Bhairam '161, the method includes the steps of (a) extracting cannabinoids from the Cannabis plant; and (b) admixing the cannabinoids into a coffee product. The disclosed methods in Bhairam '161 produce coffee products that possesses the benefits of both coffee and Cannabis plant, plus the methods can be used to produce different coffee products including single-serve coffee pods, ground coffee, and espresso, further the methods are used to make coffee products with desired and consistent amount of tetrahydrocannabinol (THC). This not yet approved patent application of Bhairam '161 is a continuation of Bhairam '865 meaning that is has the same base content—but different claims which specify levels of THC plus caffeine, including tea, and separate out the maltodextrin and propylene glycol.

Next, in the coffee/cannabinoid prior art in United States Patent Application Publication Number 2016/0324776 to Glatzel disclosed is a caffeinated drink with cannabinoids, wherein the drink retains its original taste and appearance. This application to Glatzel also discloses coffee powder with cannabinoids, roasted coffee beans with cannabinoids, and loose tea leaf with cannabinoids. Further in Glatzel disclosed are methods to the make and use of the above caffeinated drinks, coffee powder, coffee beans, and loose tea leaf. Glatzel is close to Benson minus the K-Cup part, however, adding tea.

Continuing, in the coffee/cannabinoid prior art in U.S. Pat. No. 9,629,886 to Franklin, et al. disclosed is a method for producing powderized cannabis oil, and the resulting powderized cannabis oil, in which concentrated cannabis oil is mixed with and absorbed by a modified starch powder, preferably maltodextrin, in a ratio of at least three grams of starch powder for every one-eighth of a gram of cannabis oil is disclosed. Further disclosed in Franklin are beverages, baked goods, and single-serve beverage brewing cartridges utilizing or incorporating the powderized cannabis oil to create human-consumable products that contain an emulsified, tasteless, and odorless dose of cannabis oil. Franklin is concerned with making the cannabis oil into a multi-use powder form for use in drinks to overcome the problem in emulsifying oils in liquids in addition to other foods.

In summary, this gives an example of the current state of the art in the cannabinoid Coffee arts, wherein Bhairam is related to the actual coffee product itself (K-Cups), and a specific method of cannabinoid extraction (CO2), using maltodextrin (synthetic food starch), and propylene glycol (RV Antifreeze). Benson is more concerned with K-cup manufacture with added flavorings, plus a process of decarboxylating from cannabis. The patent application publication of Bhairam '161 is a continuation of Bhairam '865 meaning that is has the same base content-but different claims which specify levels of tetrahydrocannabinol plus caffeine, including tea, and separate out the maltodextrin and propylene glycol. Glatzel is also a patent application publication that is close to Benson minus the K-Cup part, however, adding tea. Franklin is concerned with making the cannabis oil into a multi-use powder form for use in drinks to overcome the problem in emulsifying oils in liquids in addition to other foods.

Even though the use of cannabidiol (termed CBD) in food and drink is well known, however, the above disclosed prior art did not have any specific teachings related to use of CBD in creamers for drinks. What is needed is a composition for use as a creamer that utilizes the inherent benefits of cannabidiol (CBD) that is termed one of the non-psychotropic cannabinoids that has been shown to help with alcohol tolerance, attenuation of; nausea, vomiting, gastrointestinal tract distress, and headaches, plus has antioxidant properties in humans, and further helps to ward off anxiety and depression. Thus, producing a human consumable drink additive in the form of a creamer with CBD, wherein the CBD would act to lessen the negative effects of headache, nausea, and gastrointestinal tract distress would be desirable.

As distilled from Wikipedia for a background on an application of CBD, CHARLOTTE'S WEB is a high-cannabidiol (CBD), low-tetrahydrocannabinol (THC) Cannabis extract marketed as a dietary supplement under federal law of the United States and medical cannabis under state laws. CBD does not induce the psychoactive "high" typically associated with recreational marijuana strains that are high in THC, as CBD typically contains less than 0.3% THC CHARLOTTE'S WEB is named after Charlotte Figi, born Oct. 18, 2006 (age 10), whose story has led to her being described as "the girl who is changing medical marijuana laws across America". Her parents and physicians say she experienced a reduction of her epileptic seizures brought on by Dravet syndrome after her first dose of medical marijuana at five years of age. Her usage of CHARLOTTE'S WEB was first featured in the 2013 CNN documentary "Weed". Media coverage increased demand for CHARLOTTE'S WEB and similar products high in CBD, which has been used to treat epilepsy in toddlers and children. It was originally called "Hippie's Disappointment" as it was a strain that had high CBD instead of THC.

Charlotte Figi developed Dravet syndrome (also known as severe myoclonic epilepsy of infancy or SMEI) as a baby. By age three, Figi was severely disabled and having 300 grand mal seizures a week despite treatment. Her parents learned about another child with Dravet Syndrome, who had been using a different type of medical marijuana since June 2011, and decided to try marijuana. Her parents and physicians said that she improved immediately. She now follows a regular regimen that uses a solution of the high-CBD marijuana extract in olive oil. She is given the oil under her tongue or in her food. Her parents said in 2013 that her epilepsy had improved so that she had only about four seizures per month, and she was able to engage in normal childhood activities The CBD now named after Figi was not the first type her parents tried. As their original supply, a type called R4 that is also high in CBD and low in THC, was running out, they contacted the Stanley brothers. From the Stanley's' stock, they chose the high-CBD variety that has since been renamed to CHARLOTTE'S WEB as credited to the Stanley Brothers and a trademark of the Stanley Brothers.

Charlotte's story has been featured on two CNN documentaries, THE DOCTORS TV SHOW, 60 MINUTES AUSTRALIA, and DATELINE NBC among many other sources. An article in the NATIONAL JOURNAL detailing the role of several children as uniquely powerful advocates for medicinal pot across the country described Charlotte as the first poster child for the issue. Her story has led to her being described as "the girl who is changing medical marijuana laws across America", as well as the "most famous example of medicinal hemp use".

The state of Colorado has legalized both the Medicinal and Recreational use of marijuana, and many parents have flocked there with their suffering children in search of CHARLOTTE'S WEB and other forms of medical marijuana. In November 2013, CBS Denver reported that there is now a growing community of 93 families with epileptic children using marijuana daily. Hundreds are on a waiting list and thousands are calling. In October 2014, it is noted that the Stanley brothers had a waiting list of more than 12,000 families. They have been termed "marijuana refugees" part of a migration of families uprooting their lives and moving to Colorado, where the medicinal use of marijuana is permitted being forced to flee states where cannabis is off limits.

Families who say they have run out of pharmaceutical options have moved to Colorado to access CHARLOTTE'S WEB. The demand has spurred calls for more research to determine whether these products actually do what is claimed. Amy Brooks-Kayal, vice president of the American Epilepsy Society, stated that epileptic seizures may come and go without any obvious explanation, and that CHARLOTTE'S WEB could cause developmental harm. She recommended that parents relocate so that their affected children could have access to one of the nation's top pediatric epilepsy centers rather than move to Colorado.

CBD has been shown to help quiet hyperactivity in the brain. With over 1,200 peer reviewed journals, a number of doctors are calling CBD oil the most exciting ingredient being researched today. Also that it has been prescribed by American doctors for Post Traumatic Stress Disorder (PTSD), Obsessive Compulsive Disorder (OCD), Attention Deficit Disorder (ADD), and also Chronic Traumatic Encephalopathy (CTE). The National Football League (NFL) is studying CBD as a supplement to combat the painful brain activity as a result of being hit in the head too many times.

The desired serving size is designed to deliver a clinical dosage, 10 mg. of CBD or industrial (non-psychoactive) hemp extract oil.

SUMMARY OF INVENTION

Broadly, the present invention is of the cannabinoid enriched creamer composition for human consumption, the composition includes by weight about thirty-five point three-three percent (35.33%) coconut oil, about thirteen point five-eight percent (13.58%) ghee, about thirty-two point six percent (32.6%) goats milk powder, about five point eight-five percent (5.85%) vanilla powder, about one point three-four percent (1.34%) stevia extract, about point three-eight percent (0.38%) sunflower lecithin, and about ten point nine two percent (10.92%) cannabinoid in a liquid state.

These and other objects of the present invention will become more readily appreciated and understood from a consideration of the following detailed description of the exemplary embodiments of the present invention.

REFERENCE NUMBERS IN DRAWINGS

50 Cannabinoid enriched creamer composition that includes components 55, 60, 65, 70, 75, 80, and 85
55 Coconut oil at about thirty-five point three-three percent (35.33%) by weight of the cannabinoid enriched creamer composition 50
60 Ghee at about thirteen point five-eight percent (13.58%) by weight of the cannabinoid enriched creamer composition 50
65 Goats milk powder thirty-two point six percent (32.6%) by weight of the cannabinoid enriched creamer composition 50
70 Vanilla powder at about five point eight-five percent (5.85%) by weight of the cannabinoid enriched creamer composition 50
75 Stevia extract at about one point three-four percent (1.34%) by weight of the cannabinoid enriched creamer composition 50
80 Sunflower lecithin at about point three-eight percent (0.38%) by weight of the cannabinoid enriched creamer composition 50
85 Cannabinoid in a liquid state at about ten point nine two percent (10.92%) by weight of the cannabinoid enriched creamer composition 50
86 Cannabidiol (CBD) being the non-psychotropic cannabis constituent species of the genus of cannabinoid 85
87 Cannabidiol oil (CBD oil) is where cannabidiol 86 is dissolved in a medium of a human consumable oil that allows for varying percentages of cannabidiol 86 concentration by weight within the oil
88 Cannabinol (CBN) is the primary product of THC 175 degradation with little of this existing in a fresh cannabis plant
90 Kit for a human consuming the cannabinoid enriched creamer composition 50
95 Self stirring coffee cup
100 Human consumable drink
105 Base of the self stirring coffee cup 95
110 Surrounding sidewall of the self stirring coffee cup 95
115 Margin of the surrounding sidewall 110
120 Open aperture of the margin 115
125 Interior of the base 105 and surrounding sidewall 110
130 Agitator structure of the self stirring coffee cup 95
135 Movement of the agitator structure 130
140 Means for imparting movement 135 to the agitator structure 130
145 Motor of the means 140 for imparting movement 135 to the agitator structure 130
150 Handle of the self stirring coffee cup 95
155 On/off switch disposed on the handle 150
160 Human consumable drink
165 Mixing or agitation of the cannabinoid enriched creamer composition 50 and the human consumable drink 160
170 Homogenous mixture of the cannabinoid enriched creamer composition 50 and the human consumable drink 160
175 Tetrahydrocannabinol (THC)
180 Cannabis plant
185 Cannabis plant hemp
190 Cannabis plant marijuana
195 Cavitation
200 Hemp
205 Plant based
210 Psychoactive
215 Synthetic based Definitions AGITATION 165—is when a velocity is created within the mixture 170 via passing a blade 130 through the mixture 170 at a velocity greater that the mixture itself or alternatively via imparting movement to the self stirring coffee cup 95 at a velocity greater that the mixture 170 itself.

CANNABIDIOL 86—(CBD) being the non-psychotropic cannabis constituent, is preferably derived from hemp in a liquid state, with a melting point of about sixty-six (66) degrees Celsius and above. Hemp being defined as having less than about zero point three (0.3) percent % THC. Cannabidiol is a non-psychoactive cannabinoid 85 that helps to avoid toxicity that is encountered with psychoactive cannabinoids. There are numerous cannabinoids that have been isolated from the cannabis plant.

CANNABIDIOL OIL 87—(CBD OIL) is where cannabidiol is dissolved in a medium of a human consumable oil that allows for varying percentages of cannabidiol concentration by weight within the oil, the oil typically is a byproduct of cannabidiol extraction from usually an industrial hemp plant being hemp oil extracts and fatty acids. Thus, the typical purity by weight of cannabidiol 85 to the oil of cannabidiol oil 85 is about five (5) to fifty (50) percent.

CANNABINOIDS 85—are a group of chemical compounds that act upon the cannabinoid receptors in cells that are primarily in the brain which can include cannabinol, THC, or cannabidiol that is found in cannabis saliva (Marijuana) in the form of a phytocannabinoid (termed tetrahydrocannabinol or THC) being the psychoactive compound of cannabis or in the form of a synthetic cannabinoid. Two of the cannabinoids 85 defined here are CBD 86, 87 and CBN 88. Thus cannabinoids 85 are the genus and CBD 86, 87 and CBN 88 are some of the species of the genus of the cannabinoids 85.

CANNABINOL 88—(CBN) is the primary product of THC 175 degradation with little of this existing in a fresh cannabis plant, the aforementioned THC degradation is caused primarily from THC exposure to light and air over time, CBN is only mildly psychoactive.

CANNABIS PLANT 180—there are two major variants of the cannabis plant, the first is for Hemp and the second is for THC 175, wherein for the hemp variant the cannabis plants are tall growing (stalk focused with minimal leaves) and contain a lower content of THC 175, typically being in the range of about point zero five percent (0.05) % to one percent (1) % THC levels and the THC 175 variant of cannabis plants are lower growing (with maximum number of leaves) and have a higher THC content, typically being in the range of about five percent (5) % to thirty percent (30) % THC 175 levels.

CANNABIS PLANT (HEMP) 185—tall growing and having long fibrous stalks with few number of leaves and buds grown for hemp oil, wax, resin, hemp seed food, animal feed, cloth, and rope having low THC 175 content typically being in the range of about point zero five percent (0.05) % to one percent (1) % THC 175 levels. Note that CBD OIL 87 can be extracted from hemp plants with the resulting low THC 175 levels.

CANNABIS PLANT (MARIJUANA) 190—low growing and bushy with large number of leaves and buds grown for high THC 175 content typically being in the range of about five percent (5) % to thirty percent (30) % THC 175 levels. Note that CBD OIL 87 can be extracted from marijuana plants 190 with the resulting high THC 175 levels.

CAVITATION 195—the formation of a gas pocket within a liquid caused by the rapid movement of a blade through a liquid, wherein the rapid blade movement causes a local pressure reduction in the liquid that results in a local liquid phase change from liquid to gas causing ineffective agitation and potential blade surface damage.

COMPOSITION 50—the cannabinoid enriched creamer composition that is preferably in the form of the cannabidiol oil 87 including the other components by weight as previously stated for the coconut oil 55, ghee 60, goats milk powder 65, vanilla powder 70, stevia extract 75, and sunflower lecithin 80.

HEMP 200—products of the Hemp variant cannabis plant that include fiber, oil, and seed.

HOMOGENUS MIXTURE 170—as between the cannabinoid enriched creamer composition 50 and the human consumable drink 160, the cannabidiol oil 87 is fully or partially emulsified within the human consumable drink 160 or in other words when the cannabidiol oil 87 is diffused in the human consumable drink 160.

PLANT BASED 205—extracts such as CBD 86, CBN 88, or THC 175 that are derived from cannabis plants.

PSYCHOACTIVE 210—means cannabinoid brain receptor mediated psychoactivity that includes effects of euphoria, lightheadedness, reduced motor skills, and memory impairment. Psychoactivity does not include non-cannabinoid receptor mediated effects such as the anxiolytic effect of CBD 86, being generally decreased subjective anxiety and increased mental sedation, thus differentiating the psychological effects of THC 175 versus CBD 86.

SYNTHETIC BASED 215—Chemical constructions such as CBD, CBN, or THC that are not derived from cannabis plants. However, the chemical construction and effect upon the user can be different in a negative way than plant based extractions of CBD 86, CBN 88, or THC 175.

TETRAHYDROCANNABINOL 175—(THC) is the principal psychoactive constituent or cannabinoid of cannabis plants.

DETAILED DESCRIPTION

Figure 1:
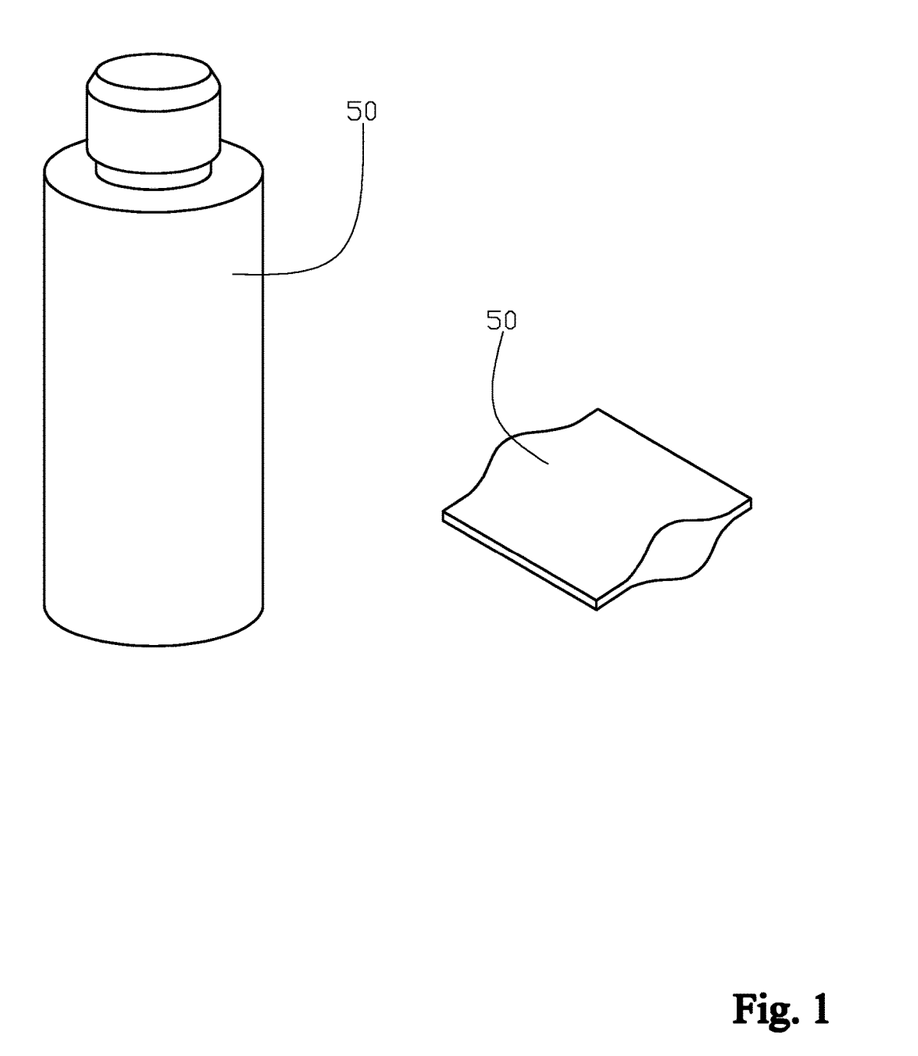
FIG. 1 shows the packaging options for the cannabinoid enriched creamer composition in either a twenty four serving bottle or a single serving packet.
Figure 2:
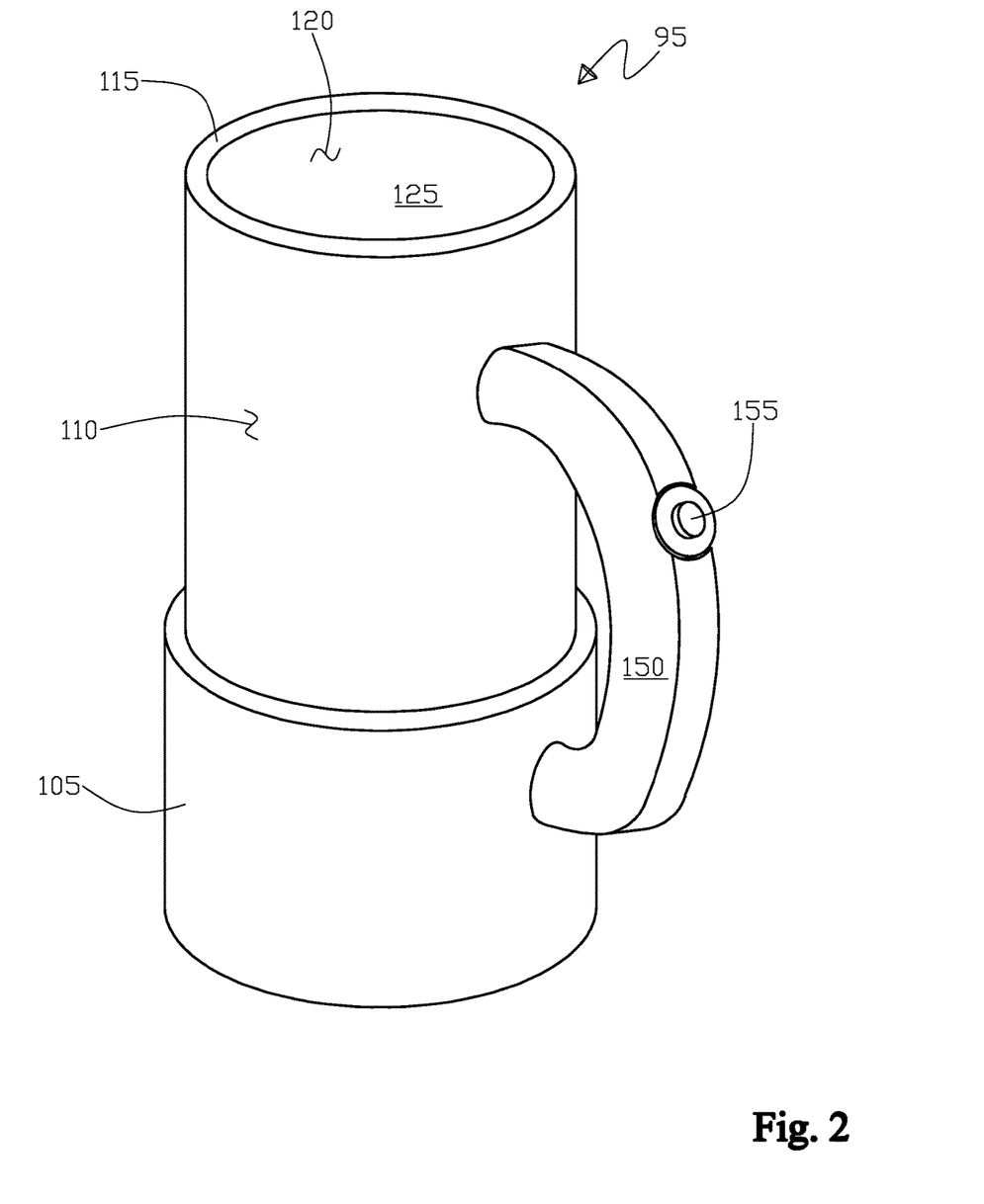
FIG. 2 shows an upper perspective view of a self stirring coffee cup that includes a base, a surrounding sidewall, wherein the sidewall terminates in a margin that forms an open aperture, wherein the base and sidewall define an interior, also shown is a handle with an on/off switch.

Starting with initial reference to FIG. 1 shown are the packaging options for the cannabinoid enriched creamer composition 50 in either a twenty four serving bottle or a single serving packet. Next, FIG. 2 shows an upper perspective view of the self stirring coffee cup 95 that includes a base 105, a surrounding sidewall 110, wherein the sidewall 110 terminates in a margin 115 that forms an open aperture 120, wherein the base 105 and sidewall 110 define an interior 125, also shown is a handle 150 with an on/off switch 155.

Figure 3:
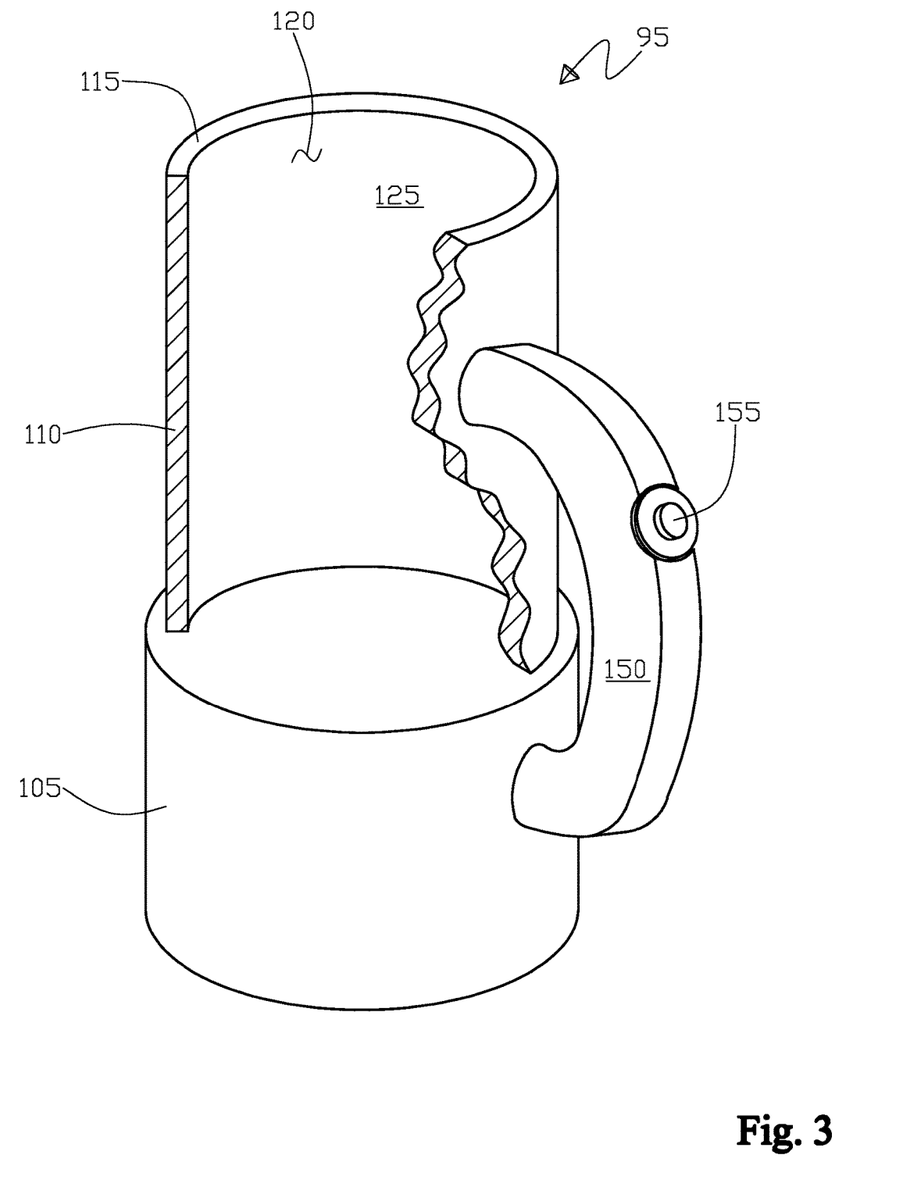
FIG. 3 shows a cut-away upper perspective view of the self stirring coffee cup that includes the base, the surrounding sidewall, wherein the sidewall terminates in the margin that forms the open aperture, wherein the base and sidewall define the interior, also shown is the handle with the on/off switch, wherein the interior and base are shown.

Continuing, FIG. 3 shows a cut-away upper perspective view of the self stirring coffee cup 95 that includes the base 105, the surrounding sidewall 110, wherein the sidewall 110 terminates in the margin 115 that forms the open aperture 120, wherein the base 105 and sidewall 110 define the interior 125, also shown is the handle 150 with the on/off switch 155, wherein the interior 125 and base 105 are shown.

Figure 4:
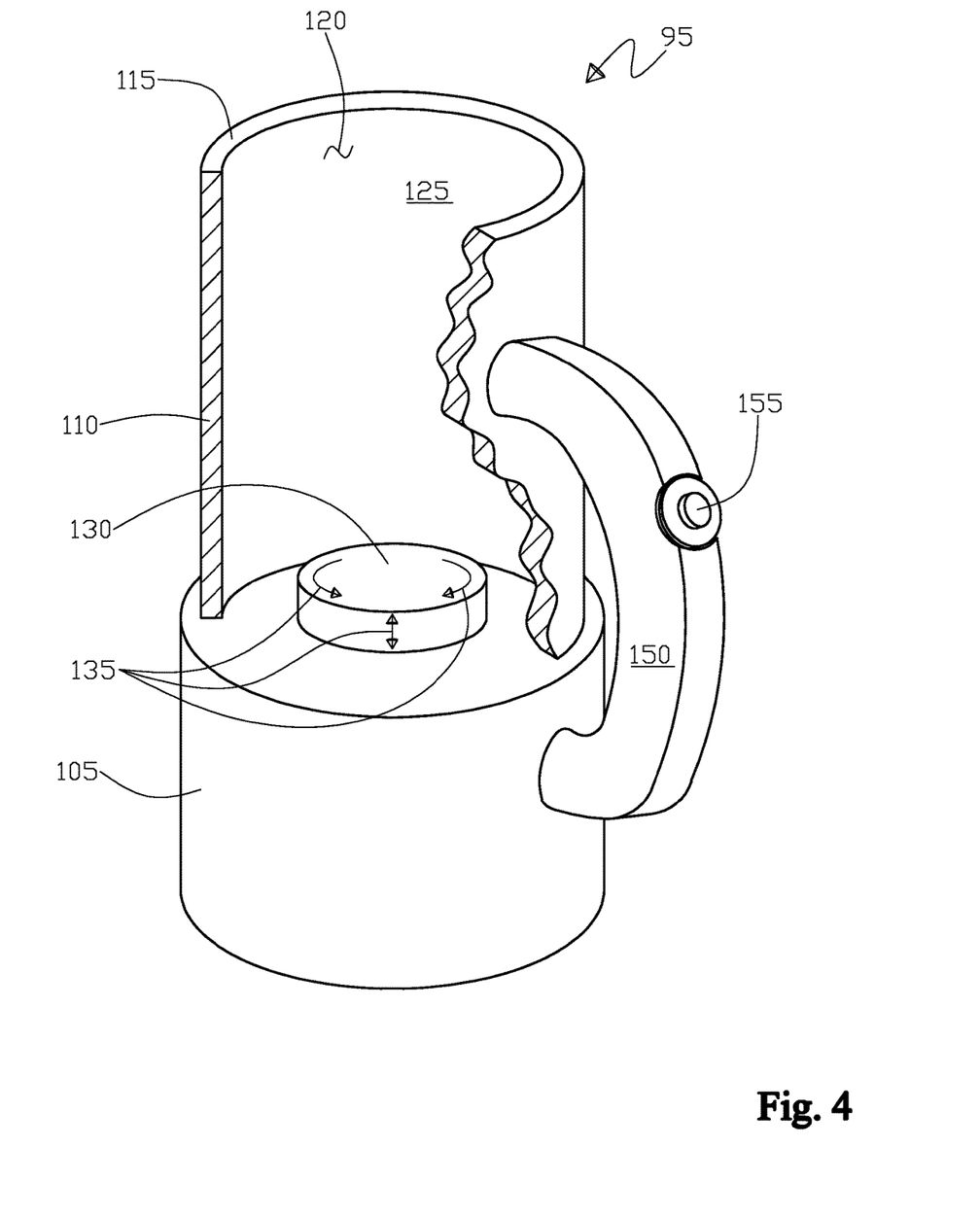
FIG. 4 shows a cut-away upper perspective view of the self stirring coffee cup that includes the base, the surrounding sidewall, wherein the sidewall terminates in the margin that forms the open aperture, wherein the base and sidewall define the interior, also shown is the handle with the on/off switch, wherein the interior, base, and agitator structure, plus movement of the agitator structure are shown.

Further, FIG. 4 shows a cut-away upper perspective view of the self stirring coffee cup 95 that includes the base 105, the surrounding sidewall 110, wherein the sidewall 110 terminates in the margin 115 that forms the open aperture 120, wherein the base 105 and sidewall 110 define the interior 125, also shown is the handle 150 with the on/off switch 155, wherein the interior 125, base 105, and agitator structure 130, plus movement 135 of the agitator structure 130 are shown.

Figure 5:
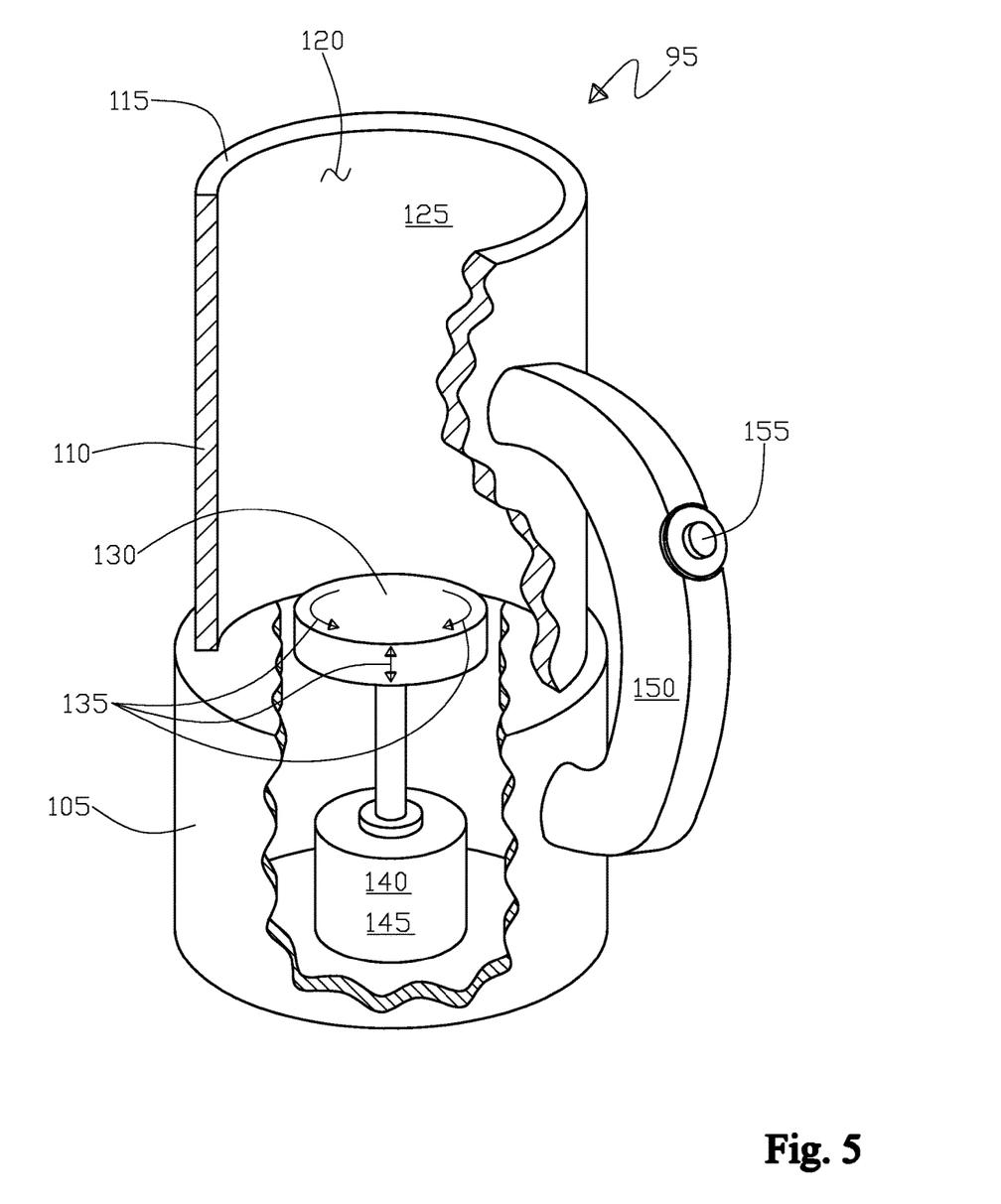
FIG. 5 shows a cut-away upper perspective view of the self stirring coffee cup that includes the base, the surrounding sidewall, wherein the sidewall terminates in the margin that forms the open aperture, wherein the base and sidewall define the interior, also shown is the handle with the on/off switch, wherein the interior, base, and agitator structure, plus movement of the agitator structure are shown as driven by a means for imparting movement to the agitator structure in the form of a motor.

Moving onward, FIG. 5 shows a cut-away upper perspective view of the self stirring coffee cup 95 that includes the base 105, the surrounding sidewall 110, wherein the sidewall 110 terminates in the margin 115 that forms the open aperture 120, wherein the base 105 and sidewall 110 define the interior 125, also shown is the handle 150 with the on/off switch 155, wherein the interior 125, base 105, and agitator structure 130, plus movement 135 of the agitator structure 130 are shown as driven by the means 140 for imparting movement 135 to the agitator structure 130 in the form of a motor 145.

Figure 6:
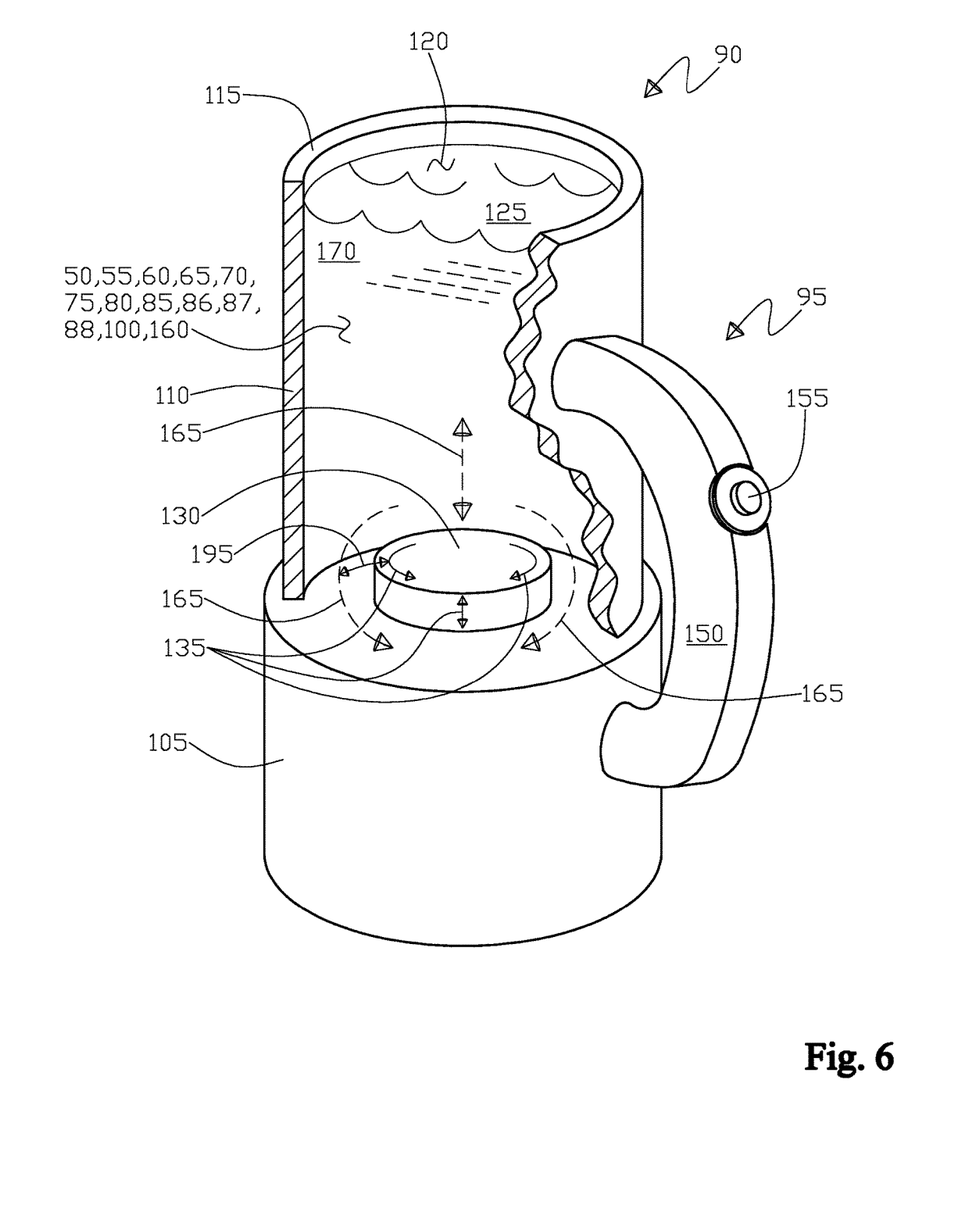
FIG. 6 shows a cut-away upper perspective view of the self stirring coffee cup that includes the base, the surrounding sidewall, wherein the sidewall terminates in the margin that forms the open aperture, wherein the base and sidewall define the interior, also shown is the handle with the on/off switch, wherein the interior, base, and agitator structure, plus movement of the agitator structure are shown, wherein the cannabinoid enriched creamer composition and a human consumable drink are disposed within the interior wherein the agitator structure mixes the cannabinoid enriched creamer composition and the human consumable drink.

Continuing, FIG. 6 shows a cut-away upper perspective view of the self stirring coffee cup 95 that includes the base 105, the surrounding sidewall 110, wherein the sidewall 110 terminates in the margin 115 that forms the open aperture 120, wherein the base 105 and sidewall 110 define the interior 125, also shown is the handle 150 with the on/off switch 155. Further FIG. 6 shows the interior 125, base 105, and agitator structure 130, plus movement 135 of the agitator structure 130 are shown, wherein the cannabinoid enriched creamer composition 50 and a human consumable drink 100 are disposed within the interior 125, wherein the agitator structure 130 mixes 165 the cannabinoid enriched creamer composition 50 and the human consumable drink 100.

Broadly, the present invention is of the cannabinoid enriched creamer composition 50 for human consumption, the composition 50 includes by weight about thirty-five point three-three percent (35.33%) coconut oil 55, about thirteen point five-eight percent (13.58%) ghee 60, about thirty-two point six percent (32.6%) goats milk powder 65, about five point eight-five percent (5.85%) vanilla powder 70, about one point three-four percent (1.34%) stevia extract 75, about point three-eight percent (0.38%) sunflower lecithin 80, and about ten point nine two percent (10.92%) cannabinoid 85 in a liquid state.

Optionally for the cannabinoid enriched creamer composition 50, wherein the genus of cannabinoid 85 is preferably a species of cannabidiol 86. Further, for the cannabinoid enriched creamer composition 50, the species of cannabidiol 86 is preferably is selected from the group consisting of plant based 205, synthetic based 215, and a combination of plant 205 plus synthetic based 215.

Also optionally for the cannabinoid enriched creamer composition 50, the cannabidiol 86 is non-psychoactive 210. Further, optionally for the cannabinoid enriched creamer composition 50, the cannabidiol 86 is preferably derived from an industrial hemp plant 200.

Continuing, optionally for the cannabinoid enriched creamer composition 50, the cannabidiol 86 is preferably a cannabidiol oil 87 that has a concentration of about a point one-seven percent (0.17%) by weight cannabidiol 86 content.

In addition, optionally for the cannabinoid enriched creamer composition 50, the cannabidiol 86 has no more than zero point three percent (0.3%) of tetrahydrocannabinol 175 content to reduce a psychoactive effect.

Looking at FIGS. 1 to 6, a kit 90 is disclosed for a human consuming the cannabinoid enriched creamer composition 50, wherein the kit includes the cannabinoid enriched creamer composition 50 as previously described and a self stirring coffee cup 95.

Looking in particular at FIGS. 2 to 6, for the kit 90 for a human consuming the cannabinoid enriched creamer composition 50, wherein the self stirring coffee cup 95 is constructed of a base 105 and a surrounding sidewall 110 extending from the base 105 wherein the sidewall 110 terminates in a margin 115 forming an open aperture 120 being disposed opposite of the base 105. Wherein, the base 105 and sidewall 110 are defining an interior 125, further the self stirring cup 95 includes an agitator structure 130 disposed within the interior 125, see in particular FIGS. 4 to 6.

Continuing, optionally on the kit 90 for a human consuming a cannabinoid enriched creamer composition 50, wherein the agitator structure 130 can further comprises a means 140 for imparting movement 135 to the agitator 130 relative to the base 105 and sidewall 110, as best shown in FIGS. 4 to 6. Further optionally, for the means 140 for imparting movement 135 to the agitator 130 can be preferably constructed of a motor 145, see FIG. 5 in particular.

The agitator structure 130 can take on a number of forms from being a disc to having notches on the periphery or surface of the disc, to being a bladed propeller, basically any structure that agitates the liquid that the agitator 130 is immersed in. Noting that the agitator 130 could be used with only manual agitation movement 135 being without the means 140 for imparting movement 135 to the agitator 130 relative to the base 105 and sidewall 110, thus with the manual only agitation movement 135 being similar to a spray paint can internal agitator ball that assists in the manual agitation of the paint.

Further for the means 140 for imparting movement 135 to the agitator 130 relative to the base 105 and sidewall 110, the means 140 could be anything that is capable of imparting the movement 135 which itself could be rotational (bi-rotational rotation and/or uni-directional rotation), and/or axial movement all separately or combined in any manner. The means 140 could be a motor 145 electrical or otherwise such as flywheel, spring, fluid pressure, and so on. Noting that the movement 135 speed or velocity is limited by the risk of cavitation 195 that could introduce undesirable air bubbles into the cannabinoid enriched creamer composition 50 and human consumable drink 160 and risk surface pitting damage to the agitator structure 130.

Another option for the kit 90 for a human consuming the cannabinoid enriched creamer composition 50, wherein the kit 90 can further comprise a human consumable drink that is coffee. Further, an option for the kit 90 for a human consuming the cannabinoid enriched creamer composition 50, wherein the kit 90 can further comprise a human consumable drink that is tea.

Yet, another option for the kit 90 for a human consuming the cannabinoid enriched creamer composition 50, wherein the kit 90 can further comprise a human consumable drink that is selected from the group consisting essentially of fruit flavored compositions, vegetable flavored compositions, flower flavored compositions, and seed flavored compositions.

The cannabinoid enriched creamer composition 50 is designed to make "bullet" style coffee or termed "bulletproof" coffee that is coffee blended with butter being derived from yak butter tea in Tibet, wherein broadly; unsalted butter is used combined with a medium chain triglyceride (MCT) oil, wherein the taste is similar to a creamy latte with typical claims of more energy, hunger suppression, weight loss, and enhanced mental focus from consumers.

Further to the bullet style coffee in the present invention composition 50 the components are further described as follows; the coconut oil 55 preferably having about sixty-five (65%) pure MCT oil. MCT oil is preferred as it is easier to digest than long chain triglyceride (LCT) oil. MCT gives an individual a feeling of fullness, helps maintain body weight, plus gives an individual more energy, helps an individual think more clearly, balances hormones, and contains anti-oxidant properties.

Continuing, for the ghee 60 it is high in fat soluble vitamins, A, D, E, & K2, plus ghee is rich in omega 3 & 6 fatty acids, ghee is suitable for individuals with lactose sensitivities, as ghee contains Butyrale, an essential detoxifier and anti inflammatory, in addition ghee supports weight loss because it initiates a natural fat burning response in the individuals' body.

Next, goats milk powder 65 is superior to cow's milk, goats milk is easier to digest, results in less inflammation, has higher calcium, and more fatty acids but lower in cholesterol than cow's milk, also goat's milk has vitamins A, b2, C, & D.

Further, the vanilla powder 70 contains magnesium being a vital mineral that regulates an individual's nervous system, also magnesium promotes a healthy mood and metabolism, further the vanilla powder contains potassium which regulates and balances blood pressure and the electrolytes in an individual's body, it also has calcium that promotes bone health & strength. Vanilla 70 is also an aphrodisiac—great for libido and enhancing sex hormones, plus releases oxytocin and dopamine, to help with a feeling of euphoria.

Yet further for the stevia extract 75 it is a natural sweetener that does not contribute to calories or carbohydrates, stevia does not affect blood glucose or an insulin response.

Yet further, the sunflower lecithin 80 improves cholesterol levels plus also improves functions of an individual's nervous and circulatory systems, also it helps restore liver health and reverse the damaging effects of alcohol.

CONCLUSION

Accordingly, the present invention of a CANNABINOID (CBD) ENRICHED CREAMER composition and kit for consuming has been described with some degree of particularity directed to the embodiments of the present invention. It should be appreciated, though; that the present invention is defined by the following claims construed in light of the prior art so modifications or changes may be made to the exemplary embodiments of the present invention without departing from the inventive concepts contained therein.

The invention claimed is:

1. A cannabinoid enriched creamer composition for human consumption, wherein said cannabinoid enriched creamer composition lessens the negative effects of headache, nausea, gastrointestinal tract distress, and has improved flavor, said composition comprising by weight about:
 (a) thirty-five point three-three percent (35.33%) coconut oil;
 (b) thirteen point five-eight percent (13.58%) ghee;
 (c) thirty-two point six percent (32.6%) goats milk powder;
 (d) five point eight-five percent (5.85%) vanilla powder;
 (e) one point three-four percent (1.34%) stevia extract;
 (f) point three-eight percent (0.38%) sunflower lecithin; and
 (g) ten point nine two percent (10.92%) cannabinoid in a liquid state.

2. A cannabinoid enriched creamer composition according to claim 1 wherein said cannabinoid is a cannabidiol.

3. A cannabinoid enriched creamer composition according to claim 2 wherein said cannabidiol is selected from the group consisting of plant based, synthetic based, and a combination of plant plus synthetic based.

4. A cannabinoid enriched creamer composition according to claim 2, wherein said cannabidiol is non-psychoactive.

5. A cannabinoid enriched creamer composition according to claim 2, wherein said cannabidiol is derived from an industrial hemp plant.

6. A cannabinoid enriched creamer composition according to claim 5, wherein said cannabidiol is a cannabidiol oil that has a concentration of about a point one-seven percent (0.17%) by weight cannabidiol content.

7. A cannabinoid enriched creamer composition according to claim 2, wherein said cannabidiol has no more than zero point three percent (0.3%) of tetrahydrocannabinol content to reduce a psychoactive effect.

* * * * *